US010624828B2

(12) United States Patent
Kelly et al.

(10) Patent No.: US 10,624,828 B2
(45) Date of Patent: *Apr. 21, 2020

(54) PERSONAL CARE COMPOSITIONS COMPRISING A 2-PYRIDINOL N-OXIDE MATERIAL AND AN IRON CHELATOR

(71) Applicant: The Procter & Gamble Company, Cincinnati, OH (US)

(72) Inventors: Casey Patrick Kelly, Wyoming, OH (US); Gregory Scot Miracle, Liberty Township, OH (US); Patrick Christopher Stenger, Fairfield, OH (US); Charles Allen Pettigrew, Jr., West Chester, OH (US); Meng Tack Ng, Singapore (SG); Jiquan Liu, Singapore (SG); Gabriel Wei Sheng Liew, Singapore (SG); Charlie Reyes Salvador, Singapore (SG); Justin Angelo Caserta, Mason, OH (US); Jennifer Gentry Shields, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/022,863

(22) Filed: Jun. 29, 2018

(65) Prior Publication Data

US 2019/0000737 A1    Jan. 3, 2019

Related U.S. Application Data

(60) Provisional application No. 62/527,049, filed on Jun. 30, 2017.

(51) Int. Cl.
| | | |
|---|---|---|
| A61K 8/42 | (2006.01) |
| A61K 8/44 | (2006.01) |
| A61K 8/49 | (2006.01) |
| A61K 8/55 | (2006.01) |
| A61Q 19/10 | (2006.01) |
| C11D 1/00 | (2006.01) |
| C11D 3/26 | (2006.01) |
| C11D 3/28 | (2006.01) |
| C11D 3/30 | (2006.01) |
| C11D 3/33 | (2006.01) |
| C11D 7/32 | (2006.01) |
| C11D 17/00 | (2006.01) |
| A01N 37/28 | (2006.01) |
| A01N 37/44 | (2006.01) |
| A01N 43/40 | (2006.01) |
| A01N 57/20 | (2006.01) |
| A61Q 17/00 | (2006.01) |
| C11D 9/30 | (2006.01) |

(52) U.S. Cl.
CPC ............ *A61K 8/4926* (2013.01); *A01N 37/28* (2013.01); *A01N 37/44* (2013.01); *A01N 43/40* (2013.01); *A01N 57/20* (2013.01); *A61K 8/42* (2013.01); *A61K 8/44* (2013.01); *A61K 8/55* (2013.01); *A61Q 17/005* (2013.01); *A61Q 19/10* (2013.01); *C11D 9/30* (2013.01); *C11D 17/0047* (2013.01); *A61K 2800/592* (2013.01)

(58) Field of Classification Search
CPC ... A61K 8/42; A61K 8/44; A61K 8/49; A61K 8/4926; A61K 8/55; A61Q 19/10; C11D 1/00; C11D 3/26; C11D 3/28; C11D 3/30; C11D 3/33; C11D 7/32
See application file for complete search history.

(56) References Cited

U.S. PATENT DOCUMENTS

| | | | |
|---|---|---|---|
| 6,624,126 B1 | 9/2003 | Kasuga et al. | |
| 8,841,247 B2* | 9/2014 | Miracle | C11D 3/046 510/238 |
| 9,550,964 B2* | 1/2017 | Miracle | C11D 3/046 |
| 2004/0247551 A1 | 12/2004 | Yokomaku | |
| 2005/0053572 A1 | 3/2005 | Hwang | |
| 2013/0045910 A1* | 2/2013 | Miracle | C11D 3/046 510/276 |
| 2014/0154189 A1 | 6/2014 | Polson et al. | |
| 2014/0274852 A1 | 9/2014 | Jiang et al. | |

FOREIGN PATENT DOCUMENTS

| | | |
|---|---|---|
| EP | 3153151 A1 | 4/2017 |
| JP | H11269042 A | 10/1999 |
| JP | H11269043 A | 10/1999 |
| JP | 2003026546 A | 1/2003 |
| JP | 2006045126 A | 2/2006 |
| JP | 2007169233 A | 7/2007 |
| JP | 2011251923 A | 12/2011 |
| KR | 20000038214 A | 7/2000 |
| KR | 20070056207 A | 6/2007 |
| KR | 20070074690 A | 7/2007 |
| KR | 100782273 B1 | 12/2007 |
| KR | 101066797 B1 | 9/2011 |
| KR | 101114307 B1 | 2/2012 |
| WO | WO2006134160 A2 | 12/2006 |

OTHER PUBLICATIONS

International Search Report and Written Opinion of the International Searching Authority, PCT/US2018/040284, dated Sep. 19, 2018, 14 pages.
International Search Report and Written Opinion of the International Searching Authority, PCT/US2019/047613, dated Nov. 21, 2019, 15 pages.
U.S. Appl. No. 16/125,940, filed Sep. 10, 2018, Huan (NMN) Wang et al.

* cited by examiner

*Primary Examiner* — Brian P Mruk

(57) ABSTRACT

A personal care composition having an effective amount of a 2-pyridinol-N-oxide material and an effective amount of an iron chelator; wherein the combination of the iron chelator and the 2-pyridinol-N-oxide material provides high antibacterial efficacy.

15 Claims, No Drawings

PERSONAL CARE COMPOSITIONS COMPRISING A 2-PYRIDINOL N-OXIDE MATERIAL AND AN IRON CHELATOR

FIELD OF THE INVENTION

The present invention is directed to personal care compositions comprising a 2-Pyridinol N-Oxide material and an effective amount of an iron chelator.

BACKGROUND OF THE INVENTION 1-hydroxy-4-methyl-6-(2,4,4-trimethylpentyl)-2-pyridone monoethanolamine salt (often referred to as piroctone olamine), is a 2-Pyridinol N-Oxide material and is an anti-bacterial active that may be used in personal care products. Surprisingly, however, iron salt impurities can reduce the efficacy of 2-Pyridinol N-Oxide materials. Therefore, there is a need to develop products that mitigate this phenomenon and provide higher efficacy. The inventors of the present invention found that select combinations of iron chelators and 2-Pyridinol N-Oxide materials unexpectedly provide significantly higher levels of anti-bacterial activity than either material alone. Thus, by utilizing 2-Pyridinol N-Oxide materials in combination with select iron chelators, the present invention delivers compositions and products with superior anti-bacterial performance.

It has also been found that due to the synergy between the materials, lower amounts of the materials may be used to provide effective anti-microbial efficacy. This is beneficial as the materials themselves can be expensive when compared to other materials normally found in personal care products. Accordingly, utilizing 2-Pyridinol N-Oxide materials in combination with select iron chelators it may be possible to provide desired anti-microbial efficacy at a lower cost than if it were used independent of the iron chelators.

SUMMARY OF THE INVENTION

The present invention is directed to a personal care composition having an effective amount of a 2-pyridinol-N-oxide material and an effective amount of an iron chelator; wherein the combination of the iron chelator and the 2-pyridinol-N-oxide material provides high antibacterial efficacy.

DETAILED DESCRIPTION OF THE INVENTION

While the specification concludes with claims which particularly point out and distinctly claim the invention, it is believed the present invention will be better understood from the following description.

The present invention may comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

"Bar soap," as used herein, refers to compositions intended for topical application to a surface such as skin or hair to remove, for example, dirt, oil, and the like. Bar soaps can be rinse-off formulations, in which the product is applied topically to the skin or hair and then subsequently rinsed within minutes from the skin or hair with water. Bar soaps can also be wiped off using a substrate. Bar soaps can be in the form of a solid (e.g., non-flowing) bar soap intended for topical application to skin or can be in the form of a soft solid which is compliant to the body. Bar soaps can be wrapped in a substrate which remains about all or a portion of the bar during use.

"Comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

"Effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

"Personal care composition" refers to compositions intended for topical application to skin or hair. The personal care compositions can be, for example, in the form of a liquid, semi-liquid cream, lotion, gel, foam, or solid and are intended for topical application to the skin and/or hair. Examples of personal care compositions can include but are not limited to bar soaps, shampoos, conditioning shampoos, body washes, moisturizing body washes, shower gels, skin cleansers, cleansing milks, in shower body moisturizers, pet shampoos, shaving preparations, etc.

"Rinse-off" means the intended product usage includes application to skin and/or hair followed by rinsing and/or wiping the product from the skin and/or hair within a few seconds to minutes of the application step.

"STnS" refers to sodium trideceth(n) sulfate, wherein n can define the average number of moles of ethoxylate per molecule.

"Structured" refers to having a rheology that can confer stability on the personal care composition. A cleansing phase can be considered to be structured if the cleansing phase has one or more following characteristics: (a) Zero Shear Viscosity of at least 100 Pascal-seconds (Pa-s), at least about 200 Pa-s, at least about 500 Pa-s, at least about 1,000 Pa-s, at least about 1,500 Pa-s, or at least about 2,000 Pa-s; (b) A Structured Domain Volume Ratio as measured by the Ultracentrifugation Method described hereinafter, of greater than about 40%, at least about 45%, at least about 50%, at least about 55%, at least about 60%, at least about 65%, at least about 70%, at least about 75%, at least about 80%, at least about 85%, or at least about 90%; or (c) A Young's Modulus of greater than about 2 Pascals (Pa), greater than about 10 Pa, greater than about 20 Pa, greater than about 30 Pa, greater than about 40 Pa, greater than about 50 Pa, greater than about 75 Pa, or greater than about 100 Pa.

"Substantially free of" refers to about 2% or less, about 1% or less, or about 0.1% or less of a stated ingredient. "Free of" refers to no detectable amount of the stated ingredient or thing.

The term "2-pyridinol-N-oxide material" encompasses materials that include the unsubstituted 2-pyridinol-N-oxide, substituted 2-pyridinol-N-oxide and their salts and tautomeric structures.

Iron Chelators

In the present invention, iron chelators may have, but are not limited to having, the following characteristics:
1. An affinity for iron ions in either the ferrous (iron II) or ferric (III) forms;
2. Materials having the characteristics of #1 (above) that also have a denticity of four or higher (denticity is the number of groups of a molecule that bind to the iron);
3. Materials that have the characteristics of #2, above, and also:
   a. Are natural or synthetic materials;
   b. Are included in the following chemical classes:
      i. Aminophosphates;
      ii Aminocarboxylates;
      iii. Hydroxamic acids; and
      iv. Molecules representing combinations of these chemical classes.

An iron chelator may be present from the following groups:
(1) Iron chelators represented by the following structure:

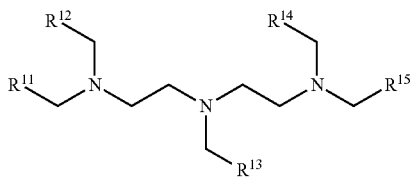

where $R^{11}$, $R^{12}$ $R^{13}$, $R^{14}$, $R^{15}$ are independently selected from the group consisting of $M^1M^2PO_3$, $CO_2M^1$, and mixtures thereof where $M^1$ and $M^2$ are independently selected from the group of H, ammonium, and a metal salt, wherein the metal salt is selected from the group consisting of sodium, potassium, calcium, magnesium, and aluminum.

(2) Iron chelators represented by the following structure:

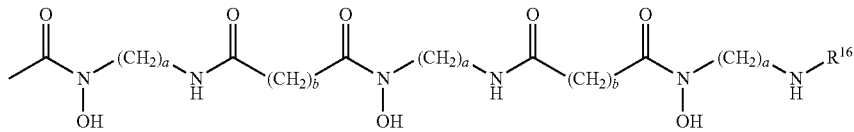

where a is an integer from 2 to 7 wherein any of the $CH_2$ groups in this unit may be substituted with alkyl or aryl units that may contain heteroatoms (S, N, O, Cl, F, Br or I), where b is an integer from 1 to 7 wherein any of the $CH_2$ groups in this unit may be substituted with alkyl or aryl units that may contain heteroatoms (S, N, O, Cl, F, Br or I), where $R^{16}$ is H or $(CH_2)_n$, where n in an integer from 1 to 6 or is a $CH_2$ linker unit that may be further substituted at any $CH_2$ group in the chain with alkyl or aryl units that may contain heteroatoms (S, N, O, Cl, F, Br, or I).

Non-limiting examples of iron chelators include diethylenetriaminepentaacetic acid (DTPA), Diethylenetriaminepentakis (methylenephosphonic acid) (DTPMP), Desferrioxamine, their salts and combinations thereof.

The personal care composition may contain from about 0.005% to about 15% of an iron chelator, from about 0.005% to about 5% of an iron chelator, from about 0.005% to about 2.5% of an iron chelator or from about 0.05% to about 2.5% of an iron chelator.

2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

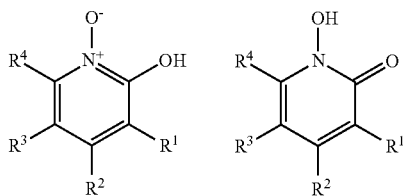

where $R^1$, $R^2$, $R^3$, $R^4$ groups are independently selected from the group consisting of H, Cl, Br, I, F, NO, $NO_2$, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $+N(R^7R^8R^9R^{10})$, and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

The 2-pyridinol-N-oxide material may be a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1.

The 2-pyridinol-N-oxide material may be a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

The 2-pyridinol-N-oxide material may be the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, ½ $Mg^{2+}$, or ½ $Ca^{2+}$, substituted ammonium, such as $C_1$-$C_6$ alkanolammnonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

The 2-pyridinol-N-oxide material may be of a substituted or unsubstituted 2-pyridinol-N-oxide material. Salts for use herein include those formed from the polyvalent metals barium, bismuth, strontium, copper, zinc, cadmium, zirconium and mixtures thereof.

The 2-pyridinol-N-oxide material may be selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, Mo.) and/or Aces Pharma (Branford, Conn.).

The 2-pyridinol-N-oxide material may be a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

The 2-pyridinol-N-oxide material may be a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

The 2-pyridinol-N-oxide material may be a 2-pyridinol-N-oxide material or tautomer thereof according to the formula(s) below:

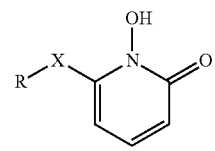

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

The 2-pyridinol-N-oxide material may be a 2-pyridinol-N-oxide material or tautomer thereof according to the formula(s) below:

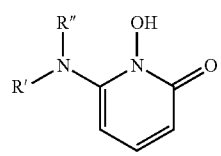

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

The personal care composition may contain from about 0.0003% to about 10%, from about 0.0003% to about 2%, from about 0.003% to about 2%, or from about 0.03% to about 1.5% of a substituted or unsubstituted 2-pyridinol N-oxide material.

As such, the personal care composition may contain from about 0.005% to about 15% of an iron chelator and from about 0.0003% to about 10% of a substituted or unsubstituted 2-pyridinol N-oxide material. The personal care composition may contain from about 0.005% to about 5% of an iron chelator and from about 0.0003% to about 2% of a substituted or unsubstituted 2-pyridinol N-oxide material. The personal care composition may contain from about 0.005% to about 2.5% of an iron chelator and from about 0.003% to about 2% of a substituted or unsubstituted 2-pyridinol N-oxide material. The personal care composition may contain from about 0.05% to about 2.5% of an iron chelator and from about 0.03% to about 1.5% of a substituted or unsubstituted 2-pyridinol N-oxide material Minimum Inhibitory Concentration (MIC)

The minimum inhibitory concentration ("MIC") is the concentration (in ppm) of anti-bacterial agent that causes growth inhibition of bacteria so that no pellet is formed in the culture medium (as explained below in the method).

To measure the growth inhibition properties of the test materials against bacteria, the protocol according to Wigand et al (*Nature Protocols* Vol. 3, No. 2, P 163-175, 2008) is followed. *Staphylococcus aureus* ATCC 6538 is cultured onto tryptic soy agar (TSA) (Oxoid CM0131) over 24 hours. The single colonies are then transferred into saline and mixed through vortex to obtain a turbidity of OD625 nm 0.08-0.13. 200 uL of this bacterial suspension is added to 19.8 mL of Mueller Hinton Broth (MHB) (BD 212322). This gives $5\times10^5$ cfu/mL.

The dilutions for the materials are then prepared and 50 uL are aliquoted into a 96 well round-bottomed plate (Nunclon™ Delta surface—Cat 163320). 50 uL of the bacteria-MHB mix is added to the 96 well round-bottomed plate thus making up 100 uL in each well. The plate is then placed into a plastic sheet to minimize evaporation. The plate is then incubated at 37° C. for 24 hours. After 24 hours, the plate is removed and read visually to determine if a pellet is formed at the bottom of the well versus positive (without adding antibacterial material) and negative (without bacterial inoculum) growth controls. Presence of a pellet in the well indicates bacteria growth (i.e. less than 100% bacteria inhibition) and conversely absence of pellet indicates 100% bacteria inhibition (i.e. no bacteria growth).

The experiment is carried out in triplicates and the MIC values are determined by the average of the results.

TABLE 1

MIC of materials against *S. aureus* ATCC 6538

| Material | MIC (ppm) |
|---|---|
| 1-hydroxy-4-methyl-6-(2,4,4-trimethylpentyl)-2-pyridone monoethanolamine salt ($MIC_{piroctone\ olamine}$) | 12.5 |
| Diethylenetriaminepentaacetic acid (DTPA) | 500 |
| Diethylenetriaminepentakis(methylenephosphonic acid) (DTPMP) | 250 |

Combinatorial Minimum Inhibitory Concentration (cMIC)

A Combinatorial Minimum Inhibitory Concentration ("cMIC") is used to determine the combinatorial effects of two chemicals on anti-bacterial activity in a tissue culture setting. Herein, the cMIC is a measure of the Minimum Inhibitory concentrations of 1-hydroxy-4-methyl-6-(2,4,4-trimethylpentyl)-2-pyridone monoethanolamine salt in combination with a chelant or vice versa.

1. Method Overview:
   a. Each cMIC assay is run in triplicates.
   b. *Staphylococcus aureus* ATCC 6538 is cultured on tryptic soy agar (TSA) (Oxoid CM0131) over 24 hours. The single colonies are then transferred into saline and mixed through vortex to obtain an optical density (OD) of 0.08-0.13 at 620 nm. 200 uL of this bacterial suspension is added to 19.8 mL of Mueller Hinton Broth (MHB) (BD 212322). This gives $5\times10^5$ cfu/mL. 100 uL of this bacteria-MHB mix is added to a 96 well flat-bottomed plate (TRP 92196).
   c. 1-hydroxy-4-methyl-6-(2,4,4-trimethylpentyl)-2-pyridone monoethanolamine salt is pipetted into the wells in varying concentrations as indicated below.
   d. Different Chelants are pipetted into the wells in varying concentrations, as indicated below.
   e. The plates are then read using a spectrophotometer at 620 nm. This is the 0-hour reading.
   f. The plates are incubated at 37° C. for 18 hours with shaking at 50 rpm.
   g. The optical density of the plate is then measured using a spectrophotometer at 620 nm.
   h. The OD value is calculated as subtraction of the readings between 18-hour and the 0-hour.
   i. cMIC is determined as the minimal concentration of 1-hydroxy-4-methyl-6-(2,4,4-trimethylpentyl)-2-pyridone monoethanolamine salt in combination with a chelant or vice versa, corresponding to the well whose OD value is less than 10% of the OD value of the control well without 1-hydroxy-4-methyl-6-(2,4,4-trimethylpentyl)-2-pyridone monoethanolamine salt and chelator (full growth).
2. Summary of Results:

TABLE 2

Combination of 1-hydroxy-4-methyl-6-(2,4,4-trimethylpentyl)-2-pyridone monoethanolamine salt with Chelator MIC and cMIC Value (ppm)

| Chelator | 1-hydroxy-4-methyl-6-(2,4,4-trimethylpentyl)-2-pyridone monoethanolamine salt | Antibacterial Efficiency of 1-hydroxy-4-methyl-6-(2,4,4-trimethylpentyl)-2-pyridone monoethanolamine salt boosted by Chelator |
|---|---|---|
| DTPMP 250# | 0 | N.A. |
| 0 | 12.5* | 0 |

TABLE 2-continued

Combination of 1-hydroxy-4-methyl-6-(2,4,4-trimethyl-pentyl)-2-pyridone monoethanolamine salt with Chelator MIC and cMIC Value (ppm)

| Chelator | | 1-hydroxy-4-methyl-6-(2,4,4-trimethylpentyl)-2-pyridone monoethanolamine salt | Antibacterial Efficiency of 1-hydroxy-4-methyl-6-(2,4,4-trimethylpentyl)-2-pyridone monoethanolamine salt boosted by Chelator |
|---|---|---|---|
| | 15.6## | 6.25** | 50% |
| | 62.5## | 3.125** | 75% |
| DTPA | 500# | 0 | N.A. |
| | 0 | 12.5* | 0 |
| | 125## | 6.25** | 50% |
| | 250## | 3.125** | 75% |

Antibacterial efficiency of 1-hydroxy-4-methyl-6-(2,4,4-trimethylpentyl)-2-pyridone monoethanolamine salt boosted by Chelator = ((MIC$_{piroctone\ olamine}$ − cMIC$_{piroctone\ olamine+chelator}$)/MIC$_{piroctone\ olamine}$) multiplied by 100%.
*(MIC$_{piroctone\ olamine}$) = is the minimum amount (PPM) of 1-hydroxy-4-methyl-6-(2,4,4-trimethylpentyl)-2-pyridone monoethanolamine salt at which there is no bacteria growth based on above method.
**is the minimum amount (PPM) of 1-hydroxy-4-methyl-6-(2,4,4-trimethylpentyl)-2-pyridone monoethanolamine salt at which there is no bacteria growth in the presence of chelant.
is the minimum amount (PPM) of chelant at which there is no bacteria growth.
is the minimum amount (PPM) of chelant at which there is no bacteria growth in the presence of 1-hydroxy-4-methyl-6-(2,4,4-trimethylpentyl)-2-pyridone monoethanolamine salt.

As shown in Table 2, the combination of 6.25 ppm 1-hydroxy-4-methyl-6-(2,4,4-trimethylpentyl)-2-pyridone monoethanolamine salt with 15.6 ppm DTPMP boosted the antibacterial efficacy of 1-hydroxy-4-methyl-6-(2,4,4-trimethylpentyl)-2-pyridone monoethanolamine salt alone by 2-fold, or 50%. The combination of 3.125 ppm 1-hydroxy-4-methyl-6-(2,4,4-trimethylpentyl)-2-pyridone monoethanolamine salt with 62.5 ppm DTPMP boosted the antibacterial efficacy of 1-hydroxy-4-methyl-6-(2,4,4-trimethylpentyl)-2-pyridone monoethanolamine salt alone by 4-fold, or 75%. The combination of 6.25 ppm 1-hydroxy-4-methyl-6-(2,4,4-trimethylpentyl)-2-pyridone monoethanolamine salt with 125 ppm DTPA boosted the antibacterial efficacy of 1-hydroxy-4-methyl-6-(2,4,4-trimethylpentyl)-2-pyridone monoethanolamine salt alone by 2-fold, or 50%. The combination of 3.125 ppm 1-hydroxy-4-methyl-6-(2,4,4-trimethylpentyl)-2-pyridone monoethanolamine salt with 250 ppm DTPMP boosted the antibacterial efficacy of 1-hydroxy-4-methyl-6-(2,4,4-trimethylpentyl)-2-pyridone monoethanolamine salt alone by 4-fold, or 75%. Each of these combinations shows that the MIC value of 1-hydroxy-4-methyl-6-(2,4,4-trimethylpentyl)-2-pyridone monoethanolamine salt in combination with the chelants disclosed is below the MIC of the antibacterial agent when used alone. For simplicity, only two concentration combinations are shown for each chelant and the antibacterial agent. However, in addition to the combinations shown, other concentrations of the antibacterial agent and chelant will provide different levels of synergy. For example, it may be desirable to boost the antibacterial efficiency by about 5%, about 10%, about 20%, about 30%, about 40%, about 60%, about 70%, about 80% or more. Such synergy levels can be obtained by adjusting the concentrations of the chelant and/or the antibacterial agent.

The ratio of chelant to antibacterial agent can also affect the antibacterial efficiency of the antibacterial agent. For example, for DTPMP, the ratio of chelant to 1-hydroxy-4-methyl-6-(2,4,4-trimethylpentyl)-2-pyridone monoethanolamine salt may be within the range from about 2.5 to about 80. Preferably, the ratio of DTPMP to 1-hydroxy-4-methyl-6-(2,4,4-trimethylpentyl)-2-pyridone monoethanolamine salt is within the range from about 2.5 to about 40 and more preferably, within the range of about 5 to about 20, and even more preferably about 20. For DTPA, the ratio of chelant to 1-hydroxy-4-methyl-6-(2,4,4-trimethylpentyl)-2-pyridone monoethanolamine salt may be within the range from about 20 to about 160. Preferably, the ratio of DTPA to 1-hydroxy-4-methyl-6-(2,4,4-trimethylpentyl)-2-pyridone monoethanolamine salt is within the range from about 20 to about 80 and more preferably, within the range of about 40 to about 80, and even more preferably about 80. Ratios outside these preferred ranges will generally provide less than the preferred synergistic effect or be less efficient in terms of the amount of each component needed to achieve the desired effect.

Iron Affinity—Log $K_1$

The strength of the association between a ligand and metal, in this case iron, can be termed iron affinity. A high iron binding affinity is required for chelators to effectively compete with iron salt impurities that reduce the efficacy of 2-pyridinol-N-oxide materials.

Affinity between a metal (M) and ligand (L) can be measured by the stepwise association constant, $K_1$ which describes the following equilibrium:

$$M + L \rightleftharpoons ML; K_1 = \frac{[ML]}{[M][L]}$$

The affinity constant is conveniently expressed as the logarithm (log $K_1$) and the larger the magnitude of this number, the stronger the association between the metal (iron ions in this case) and ligand.

TABLE 3

Iron Binding Affinities of Chelators and their MFIC Values

| Chelator | Log $K_1$[a] |
|---|---|
| Desferrioxamine | 31 |
| Diethylenetriaminepentaacetic acid (DTPA) | 28 |
| Diethylenetriaminepentakis(methylenephosphonic acid) (DTPMP) | 23 |
| Methylglycine diacetic acid (MGDA) | 16 |
| Citric Acid | 11 |

[a]NIST Standard Reference Database 46: Critically Selected Stability Constants of Metal Complexes.

The personal care composition may contain an iron chelator which has a log $K_1$ greater than about 16. The person care composition may contain an iron chelator which has a log $K_1$ greater than about 20.

Personal Care Compositions

Personal care compositions may exist in different forms. For example, a personal care composition may be in a liquid form and could be a body wash, shampoo, conditioning shampoos, body washes, moisturizing body washes, shower gels, skin cleansers, cleansing milks, in shower body moisturizers, pet shampoos, shaving preparations, etc. Personal care compositions may also be in a solid form, like in a bar soap or a semi-solid form, like a paste or gel. Solid personal care compositions can be provided in different shapes and forms, like a rectangle, oval or square, and may be in a powder or pellet form, for example. Additionally, solid and semi-solid forms may be combined with a substrate to form an article as described in more detail in U.S. Patent Application Publication Numbers 2012/0246851; 2013/0043145; 2013/0043146; and 2013/0043147.

Many personal care compositions are water-based. Water can be lost, i.e. evaporated, during a process of making a personal care composition, or subsequently, with water being absorbed by surrounding packaging (e.g. a cardboard carton), and the like. Thus, a personal care composition can also include materials that tend to bind the water such that the water can be maintained in the personal care composition at the desired levels. Examples of such materials can include carbohydrate structurants and humectants such as glycerin. However, it will be appreciated that a personal care composition can be anhydrous.

A variety of optional ingredients can also be added to a personal care composition. Such suitable ingredients can include, but are not limited to, structurants, humectants, fatty acids, inorganic salts, and other antimicrobial agents or actives.

Personal care compositions can also include hydrophilic structurants such as carbohydrate structurants and gums. Some suitable carbohydrate structurants include raw starch (corn, rice, potato, wheat, and the like) and pregelatinized starch. Some suitable gums include carregeenan and xanthan gum. A personal care composition may include from about 0.1% to about 30%, from about 2% to about 25%, or from about 4% to about 20%, by weight of the personal care composition, of a carbohydrate structurant.

Personal care compositions can also include one or more humectants. Examples of such humectants can include polyhydric alcohols. Further, humectants such as glycerin can be included the personal care composition as a result of production or as an additional ingredient. For example, glycerin can be a by-product after saponification of the personal care composition. Including additional humectant can result in a number of benefits such as improvement in hardness of the personal care composition, decreased water activity of the personal care composition, and reduction of a weight loss rate of the personal care composition over time due to water evaporation.

Personal care compositions can include inorganic salts. Inorganic salts can help to maintain a particular water content or level of the personal care composition and improve hardness of the personal care composition. The inorganic salts can also help to bind the water in the personal care composition to prevent water loss by evaporation or other means. A personal care composition can optionally include from about 0.01% to about 15%, from about 1% to about 12%, or from about 2.5% to about 10.5%, by weight of the personal care composition, of inorganic salt. Examples of suitable inorganic salts include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and tetrasodium pyrophosphate.

As noted herein, the personal care composition may include 2-Pyridinol-N-oxide materials. Such materials may be effective against gram-positive bacteria, for example, *Staphylococcus aureus*. Personal care compositions may also include one or more additional antibacterial agents that can serve to further enhance antimicrobial effectiveness of the personal care composition. For example, a personal care composition can include from about 0.001% to about 2%, from about 0.01% to about 1.5%, or from about 0.1% to about 1%, by weight of the personal care composition, of additional antibacterial agent(s). Examples of suitable antibacterial agents include carbanilides, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid, and other organic acids. Other antibacterial agents include p-chloro-m-xylenol (PCMX), 4-Isopropyl-m-cresol (IPMP), Zinc pyrithione (ZPT), Benzalkonium chloride (BZK), Didecyl dimethyl ammonium chloride (DDAC), Hinokitiol. Still other suitable antibacterial agents are described in U.S. Pat. No. 6,488,943.

Liquid Personal Care Compositions

Exemplary liquid personal care compositions include an aqueous carrier, which can be present at a level of from about 5% to about 95%, or from about 60% to about 85%. The aqueous carrier may comprise water, or a miscible mixture of water and organic solvent. Non-aqueous carrier materials may also be employed.

Such personal care compositions may include one or more detersive surfactants. The detersive surfactant component can be included to provide cleaning performance to the product. The detersive surfactant component in turn comprises anionic detersive surfactant, zwitterionic or amphoteric detersive surfactant, or a combination thereof. A representative, non-limiting, list of anionic surfactants includes anionic detersive surfactants for use in the compositions can include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the anionic surfactant can be sodium lauryl sulfate or sodium laureth sulfate. The concentration of the anionic surfactant component in the product can be any amount sufficient to provide a desired cleaning and/or lather performance, and generally ranges from about 2% to about 50%.

Amphoteric detersive surfactants suitable for use in the personal care compositions are well known in the art, and include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition are sodium 3-dodecyl-amino-propionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic detersive surfactants suitable for use in the rinse-off personal care compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants include betaines, one example of which is cocoamidopropyl betaine.

Personal care compositions may comprise one or more phases. Such personal care compositions can include a cleansing phase and/or a benefit phase (i.e., a single- or multi-phase composition). Each of a cleansing phase or a benefit phase can include various components. The cleansing phase and the benefit phase can be blended, separate, or a combination thereof. The cleansing phase and the benefit phase can also be patterned (e.g. striped).

The cleansing phase of a personal care composition can include at least one surfactant. The cleansing phase may be an aqueous structured surfactant phase and be present at from about 5% to about 20%, by weight of the personal care composition. Such a structured surfactant phase may include sodium trideceth(n) sulfate, hereinafter STnS, wherein n can define average moles of ethoxylation. For example, n can range from about 0 to about 3; from about 0.5 to about 2.7, from about 1.1 to about 2.5, from about 1.8 to about 2.2, or n can be about 2. When n is less than 3, STnS may provide improved stability, improved compatibility of benefit agents within the personal care compositions, and increased mildness of the personal care compositions, such described benefits of STnS are disclosed in U.S. patent application Ser. No. 13/157,665.

The cleansing phase can also comprise at least one of an amphoteric surfactant and a zwitterionic surfactant. Suitable amphoteric or zwitterionic surfactants (in addition to those cited herein) can include, for example, those described in U.S. Pat. Nos. 5,104,646 and 5,106,609.

A cleansing phase can comprise a structuring system. A structuring system can comprise, optionally, a non-ionic emulsifier, optionally, from about 0.05% to about 5%, by weight of the personal care composition, of an associative polymer; and an electrolyte.

The personal care composition can be optionally free of sodium lauryl sulfate, hereinafter SLS, and can comprise at least a 70% lamellar structure. However, the cleansing phase could comprise at least one surfactant, wherein the at least one surfactant includes SLS. Suitable examples of SLS are described in U.S. patent application Ser. No. 12/817,786.

As noted herein, personal care compositions can also include a benefit phase. The benefit phase can be hydrophobic and/or anhydrous. The benefit phase can also be substantially free of surfactant. A benefit phase can also include a benefit agent. In particular, a benefit phase can comprise from about 0.1% to about 50%, by weight of the personal care composition, of the benefit agent. The benefit phase may comprise less benefit agent, for example, from about 0.5% to about 20%, by weight of the personal care composition, of the benefit agent. Examples of suitable benefit agents can include petrolatum, glyceryl monooleate, mineral oil, natural oils, and mixtures thereof. Additional examples of benefit agents can include water insoluble or hydrophobic benefit agents. Other suitable benefit agents are described in U.S. patent application Ser. No. 13/157,665.

Non-limiting examples of glycerides suitable for use as hydrophobic skin benefit agents herein can include castor oil, safflower oil, corn oil, walnut oil, peanut oil, olive oil, cod liver oil, almond oil, avocado oil, palm oil, sesame oil, vegetable oils, sunflower seed oil, soybean oil, vegetable oil derivatives, coconut oil and derivatized coconut oil, cottonseed oil and derivatized cottonseed oil, jojoba oil, cocoa butter, and combinations thereof.

Non-limiting examples of alkyl esters suitable for use as hydrophobic skin benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of polyglycerin fatty acid esters suitable for use as hydrophobic skin benefit agents herein can include decaglyceryl distearate, decaglyceryl diisostearate, decaglyceryl monomyriate, decaglyceryl monolaurate, hexaglyceryl monooleate, and combinations thereof.

The personal care composition may be applied by a variety of means, including by rubbing, wiping or dabbing with hands or fingers, or by means of an implement and/or delivery enhancement device. Non-limiting examples of implements include a sponge or sponge-tipped applicator, a mesh shower puff, a swab, a brush, a wipe (e.g., wash cloth), a loofah, and combinations thereof. Non-limiting examples of delivery enhancement devices include mechanical, electrical, ultrasonic and/or other energy devices. Employment of an implement or device may help delivery of the particulate antimicrobial agent to target regions, such as, for example, hair follicles and undulations that can exist in the underarm. The personal care product may be sold together with such an implement or device. Alternatively, an implement or device can be sold separately but contain indicium to indicate usage with a personal care product. Implements and delivery devices can employ replaceable portions (e.g., the skin interaction portions), which can be sold separately or sold together with the personal care product in a kit.

Solid Personal Care Compositions

As noted herein, personal care compositions may be solid in form. Solid compositions can take many forms like powder, pellets, bars, etc. These forms will generally be described herein as bar soap, but solid composition could be in another form or shape. One example of a bar soap personal care composition can include from about 0.1% to about 35%, by weight of the personal care composition, of water, from about 45% to about 99%, by weight of the personal care composition, of soap, and from about 0.01% to about 5%, by weight of the personal care composition, of a particulate antimicrobial agent. Another suitable antimicrobial bar soap can include, for example, from about 0.1% to about 30%, by weight of the personal care composition, of water, from about 40% to about 99%, by weight of the personal care composition, of soap, and from about 0.25% to about 3%, by weight of the personal care composition, of a particulate antimicrobial agent.

Bar soap compositions can be referred to as conventional solid (i.e. non-flowing) bar soap compositions. Some bar soap compositions comprise convention soap, while others contain synthetic surfactants, and still others contain a mix of soap and synthetic surfactant. Bar compositions may include, for example, from about 0% to about 95% of a surfactant, preferably from about 20% to about 95% of a surfactant. In one example, a bar soap composition may include, for example, from about 0% to about 45% of a synthetic anionic surfactant. An example of a suitable conventional soap can include milled toilet bars that are unbuilt (i.e. include about 5% or less of a water-soluble surfactancy builder).

A personal care bar composition can include, for example from about 45% to about 99% or from about 50% to about 75%, by weight of the personal care composition, of soap. Such soaps can include a typical soap, i.e., an alkali metal or alkanol ammonium salt of an alkane- or alkene monocarboxylic acid. Sodium, magnesium, potassium, calcium, mono-, di- and tri-ethanol ammonium cations, or combinations thereof, can be suitable for a personal care composition. The soap included in a personal care composition can include sodium soaps or a combination of sodium soaps with from about 1% to about 25% ammonium, potassium, magnesium, calcium, or a mixture of these soaps. Additionally, the soap can be well-known alkali metal salts of alkanoic or alkenoic acids having from about 12 to about 22 carbon atoms or from about 12 to about 18 carbon atoms. Another suitable soap can be alkali metal carboxylates of alkyl or alkene hydrocarbons having from about 12 to about 22 carbon atoms. Additional suitable soap compositions are described in U.S. patent application Ser. No. 13/036,889.

A personal care composition can also include soaps having a fatty acid. For example, a bar soap composition could use from about 40% to about 95% of soluble alkali metal soap of $C_8$-$C_{24}$ or $C_{10}$-$C_{20}$ fatty acids. The fatty acid may, for example, have a distribution of coconut oil that can provide a lower end of a broad molecular weight range or a fatty acid distribution of peanut or rapeseed oil, or their hydrogenated derivatives, which can provide an upper end of the broad molecular weight range. Other such compositions can include a fatty acid distribution of tallow and/or vegetable oil. The tallow can include fatty acid mixtures that can typically have an approximate carbon chain length distribution of 2.5% $C_{14}$, 29% $C_{16}$, 23% $C_{18}$, 2% palmitoleic, 41.5% oleic, and 3% linoleic. The tallow can also include other mixtures with a similar distribution, such as fatty acids derived from various animal tallows and/or lard. In one example, the tallow can also be hardened (i.e., hydrogenated) such that some or all unsaturated fatty acid moieties can be converted to saturated fatty acid moieties.

Suitable examples of vegetable oil include palm oil, coconut oil, palm kernel oil, palm oil stearine, soybean oil, and hydrogenated rice bran oil, or mixtures thereof, since such oils can be among more readily available fats. One example of a suitable coconut oil can include a proportion of fatty acids having at least 12 carbon atoms of about 85%. Such a proportion can be greater when mixtures of coconut oil and fats such as tallow, palm oil, or non-tropical nut oils or fats can be used where principle chain lengths can be $C_{16}$ and higher. The soap included in a personal care composition can be, for example, a sodium soap having a mixture of about 67-68% tallow, about 16-17% coconut oil, about 2% glycerin, and about 14% water.

Soap included in a personal care composition can also be unsaturated in accordance with commercially acceptable standards. For example, a soap included in a personal care composition could include unsaturation in a range of from about 37% to about 45% of saponified material.

Soaps included in a personal care composition can be made, for example, by a classic kettle boiling process or modern continuous soap manufacturing processes wherein natural fats and oils such as tallow or coconut oil or their equivalents can be saponified with an alkali metal hydroxide using procedures well known to those skilled in the art. Soap can also be made by neutralizing fatty acids such as lauric ($C_{12}$), myristic ($C_{14}$), palmitic ($C_{16}$), or stearic ($C_{18}$) acids, with an alkali metal hydroxide or carbonate.

Soap included in a personal care composition could also be made by a continuous soap manufacturing process. The soap could be processed into soap noodles via a vacuum flash drying process. One example of a suitable soap noodle comprises about 67.2% tallow soap, about 16.8% coconut soap, about 2% glycerin, and about 14% water, by weight of the soap noodle. The soap noodles can then be utilized in a milling process to finalize a personal care composition.

Examples

The following examples are given solely for the purpose of illustration and are not to be construed as limitations of the present invention, as many variations thereof are possible without departing from the spirit and scope of the invention.

Bar soap compositions of the present invention can be made via a number of different processes known in the art. Preferably, the present compositions are made via a milling process, resulting in milled bar soap compositions. A typical milling process of manufacturing a bar soap composition includes: (a) a step in which the soap is made through either a continuous process (ConSap or continuous saponification process) or a batch-making process (i.e. neutralization process for hydrolysis fatty acid noodle or kettle process), (b) a vacuum drying step in which the soap is made into soap noodles, (c) an amalgamating step in which the soap noodles are combined with other ingredients of the bar soap composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition. Soap noodles used in the following specific examples had the following approximate proportions (%) of soap surfactants (by total weight of the soap noodles): from about 80% to about 90% anhydrous soap, which contained from about 40% to about 50% tallow (TLO), from about 30% to about 45% palm oil stearin (POS), and from about 15% to about 25% palm kernel oil (PKO) or coconut oil (CO).

Bar Soap Examples

| Ingredient | Bar Ex. 1 | Bar Ex. 2 | Bar Ex. 3 | Bar Ex. 4 | Comparative bar Ex. 1 | Comparative bar Ex. 2 |
|---|---|---|---|---|---|---|
| Soap Noodle[b] | 74.58% | 78.00% | 77.58% | 75.00% | 77.58% | 77.58% |
| Piroctone olamine[c] | 0.50% | 0.50% | 1.00% | 1.00% | 0.50% | 1.00% |
| DTPA[d] | 0.50% | — | 1.00% | — | — | — |

| Ingredient | Bar Ex. 1 | Bar Ex. 2 | Bar Ex. 3 | Bar Ex. 4 | Comparative bar Ex. 1 | Comparative bar Ex. 2 |
|---|---|---|---|---|---|---|
| DTPMP[e] 50% solution | — | 0.50% | — | 1.00% | — | — |
| Starch[f] | 18.00% | 20.00% | 20.00% | 20.00% | 20.00% | 20.00% |
| TiO$_2$[g] | 0.50% | 0.50% | 0.50% | 0.50% | 0.50% | 0.50% |
| Perfume | 1.10% | 1.10% | 1.10% | 1.10% | 1.10% | 1.10% |
| Water | Q.S. to 100 | Q.S. to 100 | Q.S. to 100 | Q.S. to 100 | Q.S. to 100 | Q.S. to 100 |
| Moisture Loss | −1.00% | −1.00% | −1.00% | −1.00% | −1.00% | −1.00% |

[b]67.2% tallow soap, about 16.8% coconut soap, about 2% glycerin and about 14% water. These percentage amounts are by weight of the soap noodle.
[c]Octopirox (1-hydroxy-4-methyl-6-(2,4,4-trimethylpentyl)-2-pyridone monoethanolamine salt) sold by Clariant
[d]Dissolvine DZ sold by Akzo Nobel
[e]Diethylenetriaminepentakis(methylenephosphonic acid), technical ~50% sold by Sigma-Aldrich
[f]NATIONAL CHA501 sold by National Starch and Chemical
[g]MT-500B sold by Tayca Corporation Liquid personal care compositions can be prepared by conventional formulation and mixing techniques. It will be appreciated that other modifications of bar soap and liquid soap compositions within the skill of those in the formulation art can be undertaken without departing from the spirit and scope of this invention. Some components may come from suppliers as dilute solutions. The amount stated reflects the weight percent of the active material, unless otherwise specified.

Liquid Soap Examples

| Ingredient | Liquid soap Ex. 1 | Liquid soap Ex. 2 | Liquid soap Ex. 3 | Liquid soap Ex. 4 | Liquid soap Ex. 5 | Liquid soap Ex. 6 |
|---|---|---|---|---|---|---|
| Sodium Laureth 3 Sulfate 28% solution[h] | 7.00% | 10.00% | 7.30% | 6.00% | 9.40% | 7.30% |
| Sodium Lauryl Sulfate 29% solution[i] | 2.20% | 4.30% | — | 2.00% | 3.30% | — |
| Cocoamidopropyl Betaine[j] | 1.90% | 2.40% | 3.50% | 0.90% | 1.40% | 3.00% |
| Sodium Benzoate[k] | 0.45% | 0.45% | 0.45% | 0.45% | 0.45% | 0.45% |
| Methylchloroisothiazolinone/methylisothiazolinone[l] | 0.05% | 0.05% | 0.05% | 0.05% | 0.05% | 0.05% |
| EDTA[m] | 0.10% | 0.10% | 0.10% | 0.10% | 0.10% | 0.10% |
| Fragrance | 0.70% | 0.70% | 0.70% | 0.70% | 0.70% | 0.70% |
| Piroctone Olamine[n] | 0.50% | 0.5% | 0.5% | 0.50% | 0.5% | 0.5% |
| DTPA[o] | 0.50% | 0.50% | 0.50% | — | — | — |
| DTPMP[p] 50% solution | — | — | — | 1.00% | 1.00% | 1.00% |
| Sodium Chloride[q] | 0-3% | 0-3% | 0-3% | 0-3% | 0-3% | 0-3% |
| Citric acid[r] | Adjust pH | Adjust pH | Adjust pH | Adjust pH | Adjust pH | Adjust pH |
| Purified water | Q.S. to 100 | Q.S. to 100 | Q.S. to 100 | Q.S. to 100 | Q.S. to 100 | Q.S. to 100 |
| pH | 4.50 | 6.00 | 6.00 | 4.50 | 6.00 | 6.00 |

Comparative Liquid Soap Examples

| Ingredient | Comparative Liquid Soap Ex. 1 | Comparative Liquid Soap Ex. 2 | Comparative Liquid Soap Ex. 3 |
|---|---|---|---|
| Sodium Laureth 3 Sulfate 28% solution[h] | 7.30% | 10.00% | 7.00% |
| Sodium Lauryl Sulfate 29% solution[i] | — | 4.30% | 2.20% |
| Cocoamidopropyl Betaine[j] | 3.50% | 2.40% | 1.90% |
| Sodium Benzoate[k] | 0.45% | 0.45% | 0.45% |
| Methylchloroisothiazolinone/methylisothiazolinone[l] | 0.05% | 0.05% | 0.05% |
| EDTA[m] | 0.10% | 0.10% | 0.10% |
| Fragrance | 0.70% | 0.70% | 0.70% |
| Piroctone Olamine[n] | 0.5% | 0.5% | 0.50% |
| DTPA[o] | — | — | — |
| DTPMP[p] 50% solution | — | — | — |
| Sodium Chloride[q] | 0-3% | 0-3% | 0-3% |

| Ingredient | Comparative Liquid Soap Ex. 1 | Comparative Liquid Soap Ex. 2 | Comparative Liquid Soap Ex. 3 |
|---|---|---|---|
| Citric acid[r] | Adjust pH | Adjust pH | Adjust pH |
| Purified water | Q.S. to 100 | Q.S. to 100 | Q.S. to 100 |
| pH | 6.00 | 6.00 | 4.50 |

[h]SLE3S sold by Stepan company
[i]SLSS sold by Tianjin Tianzhi Fine Chemical Co., Ltd
[j]AMPHOSOL HCA-HP sold by Stepan
[k]Sodium Benzoate ≥99%, FCG, FG sold by Sigma-Aldrich
[l]Kathon CG sold by Dow Chemical
[m]Obtained from Sigma Aldrich
[n]Octopirox (1-hydroxy-4-methyl-6-(2,4,4-trimethylpentyl)-2-pyridone monoethanolamine salt) sold by Clariant
[o]Dissolvine DZ sold by Akzo Nobel
[p]Diethylenetriaminepentakis(methylenephosphonic acid), technical ~50% sold by Sigma-Aldrich
[q]Adjust to desired viscosityDTPA[†]: Dissolvine DZ sold by Akzo Nobel
[r]Citric acid ACS reagent, ≥99.5% sold by Sigma-Aldrich Additional Examples/Combinations A) A personal care composition comprising:
  a) about 0.0003% to about 10% of a substituted or unsubstituted 2-pyridinol N-oxide material,
  b) about 0.005% to about 15% of a chelant,
  wherein the combination of the chelant and the substituted or unsubstituted 2-pyridinol N-oxide material increases the antibacterial efficiency of the substituted or unsubstituted 2-pyridinol N-oxide material at least about 20%, wherein the chelant is selected from the group comprising:
    (1) iron chelators represented by the following structure:

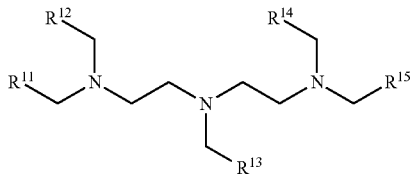

where $R^{10}$, $R^{11}$, $R^{12}$, $R^{13}$, $R^{14}$ are selected from the group consisting of $M^1M^2PO_3$, $CO_2M^1$, and mixtures thereof where $M^1$ and $M^2$ are independently selected from the group consisting of H, ammonium, and a metal salt, wherein the metal salt is selected from the group consisting of sodium, potassium, calcium, magnesium, and aluminum;
    (2) iron chelators represented by the following structure:

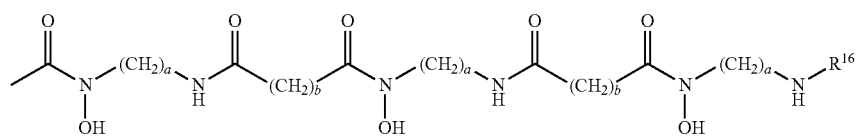

where a is an integer from 2 to 7 wherein any of the $CH_2$ groups in this unit may be substituted with alkyl or aryl units that may contain heteroatoms (S, N, O, Cl, Fe, Br or I),
  where b is an integer from 1 to 7 wherein any of the $CH_2$ groups in this unit may be substituted with alkyl or aryl units that may contain heteroatoms (S, N, O, Cl, Fe, Br or I),
  where $R^{16}$ is H or $(CH_2)_n$, where n in an integer from 1 to 6 or is a $CH_2$ linker unit that may be further substituted at any $CH_2$ group in the chain with alkyl or aryl units that may contain heteroatoms (S, N, O, Cl, F, Br, or I);
  c) from about 40% to about 95% aqueous carrier or from about 20% to about 95% by weight of at least one surfactant.

B) The personal care composition of paragraph A wherein the substituted or unsubstituted 2-pyridinol N-oxide material is present in the amount of about 0.0003% to about 2%, preferably between about 0.003% to about 2.0%, and more preferably between 0.05% and 2.5%.

C) The personal care composition of paragraphs A-B wherein the chelant is present in the amount of about 0.005% to about 5%, preferably between about 0.005% and 2.5%, and more preferably between about 0.05% and 2.5%.

D) The personal care composition of paragraphs A-C wherein the combination of the chelant and the substituted or unsubstituted 2-pyridinol N-oxide material increases the antibacterial efficiency of the substituted or unsubstituted 2-pyridinol N-oxide material at least about 50%.

E) The personal care composition of paragraph D wherein the combination of the chelant and the substituted or unsubstituted 2-pyridinol N-oxide material increases the antibacterial efficiency of the substituted or unsubstituted 2-pyridinol N-oxide material at least about 75%.

F) The personal care composition of paragraphs A-E where the iron chelator has a log $K_1$ greater than about 16.

G) The hair care composition of paragraphs A-F where the substituted or unsubstituted 2-pyridinol-N-oxide material comprises the molecular structure:

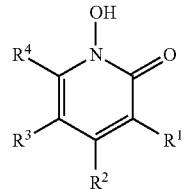

wherein $R^1$, $R^2$, $R^3$, $R^4$ are independently selected from the group consisting of H, Cl, Br, I, F, NO, $NO_2$, $(CH_2)_nG$, and mixtures thereof, wherein each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, $N(R^5R^6)$, and mixtures thereof,
wherein m is 0 or 1,
and wherein n is an integer from 0 to 4,
and wherein $R^5$ and $R^6$ are independently selected from the group consisting of H and a substituted or unsubstituted C1-C12 organic group, and
wherein $M^3$ is selected from the group consisting of H, a substituted or unsubstituted $C_1$-$C_{12}$ organic group, $+N(R^7R^8R^9R^{10})$, and 1/q M' q+ wherein M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and wherein any pair of vicinal groups, $R^1$ and $R^2$, $R^2$ and $R^3$, $R^3$ and $R^4$, may be taken together to form another five- or six-membered aromatic or aliphatic ring optionally substituted with one or more groups selected from the group consisting of Cl, Br, I, F, NO, $NO_2$, CN, $(CH_2)_n G$, and mixtures thereof.

H) The personal care composition of paragraph G, wherein each $R^1$ is independently selected from the group consisting of H, Cl, and $(CH_2)_n G$, wherein G is independently selected from the group consisting of $(O)_m SO_3 M$, $(O)_m CO_2 M$, $(O)_m C(O)(R^2)$, $(O)_m CN$, and $(O)_m (R^2)$, wherein each m is 0 or 1.

I) The personal care composition of paragraphs A-H, wherein said substituted or unsubstituted 2-pyridinol-N-oxide material is 1-hydroxy-4-methyl-6-(2,4,4-trimethylpentyl)-2-pyridone monoethanolamine salt.

J) The personal care composition of paragraphs A-I, wherein the iron chelator is diethylenetriaminepentaacetic acid (DTPA).

K) The personal care composition of paragraph J, wherein the ratio of ratio of DTPA to 1-hydroxy-4-methyl-6-(2,4,4-trimethylpentyl)-2-pyridone monoethanolamine salt is within the range from 20 to 160.

L) The personal care composition of paragraphs A-K wherein the iron chelator is Diethylenetriaminepentakis (methylenephosphonic acid) (DTPMP).

M) The personal care composition of paragraph L, wherein the ratio of chelant to 1-hydroxy-4-methyl-6-(2,4,4-trimethylpentyl)-2-pyridone monoethanolamine salt may be within the range from about 2.5 to about 80.

N) The personal care composition of paragraphs A-M, wherein the iron chelator is Desferrioxamine.

O) The personal care composition according to paragraphs A-N, wherein the composition further comprises one or more additional antibacterial agents selected from the group consisting of carbanilides, triclocarban, triclosan, halogenated diphenylether, hexachlorophene, 3,4,5-tribromosalicylanilide, and salts of 2-pyridinethiol-1-oxide, salicylic acid, other organic acids, p-chloro-m-xylenol (PCMX), 4-Isopropyl-m-cresol (IPMP), Zinc pyrithione (ZPT), Benzalkonium chloride (BZK), Didecyl dimethyl ammonium chloride (DDAC), Hinokitiol, and combinations thereof.

P) The personal care composition according to paragraphs A-O, wherein the composition comprises more than one chelant.

Q) The personal care composition according to paragraphs A-P wherein the substituted or unsubstituted 2-pyridinol N-oxide material is effective against gram-positive bacteria.

R) The personal care composition according to paragraphs A-R wherein the substituted or unsubstituted 2-pyridinol N-oxide material is effective against Staphylococcus aureus.

S) The personal care composition according to paragraphs A-S wherein the personal care composition comprises a bar soap or a body wash.

T) Use of the personal care composition according to Paragraph A-S, for treating skin.

U) Use of the personal care composition according to Paragraph A-S, for boosting the anti-bacterial performance.

V) Use according to Paragraph T, for treating cosmetically skin against Staphylococcus aureus W) Use according to Paragraph R or T, wherein the personal care composition comprises from 0.0003% to 10%, preferably from 0.0003% to 2.0%, more preferably between 0.003% and 2.0%, and more preferably between 0.03% and 1.5% of 11-hydroxy-4-methyl-6-(2,4,4-trimethylpentyl)-2-pyridone monoethanolamine salt and from 0.005% to a 15%, preferably 0.005% to 5%, more preferably 0.005% to 2.5%, and more preferably 0.05% to 2.5% of an iron chelator which is selected from the group consisting of diethylenetriaminepentaacetic acid (DTPA), Diethylenetriaminepentakis (methylenephosphonic acid) (DTPMP), Desferrioxamine, and mixtures thereof.

X) Use according to Paragraph V, wherein the ratio of chelant to 11-hydroxy-4-methyl-6-(2,4,4-trimethylpentyl)-2-pyridone monoethanolamine salt is within the range from 2.5 to 80.

Y) The personal care composition according to Paragraph A-S for use in a method of treating bacterial agents onto skin.

Z) The personal care composition according to Paragraph V, for use in a method of inhibiting the growth of Staphylococcus aureus onto skin.

AA) A method of increasing the antibacterial efficiency of a substituted or unsubstituted 2-pyridinol N-oxide material, the method comprising:
1) providing a substituted or unsubstituted 2-pyridinol N-oxide material;
2) providing a chelant selected from the group comprising:
   a) iron chelators represented by the following structure:

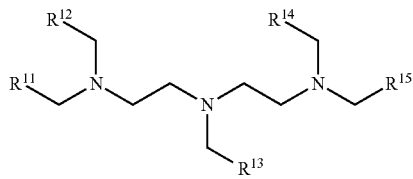

where $R^{10}$, $R^{11}$ $R^{12}$, $R^{13}$, $R^{14}$ are selected from the group consisting of $M^1 M^2 PO_3$, $CO_2 M^1$, and mixtures thereof where $M^1$ and $M^2$ are independently selected from the group consisting of H, ammonium, and a metal salt, wherein the metal salt is selected from the group consisting of sodium, potassium, calcium, magnesium, and aluminum;
   b) iron chelators represented by the following structure:

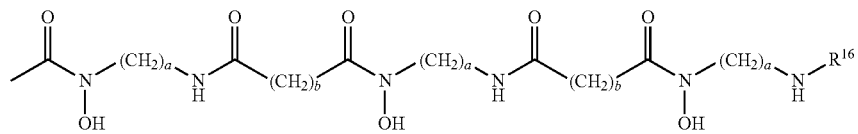

where a is an integer from 2 to 7 wherein any of the CH$_2$ groups in this unit may be substituted with alkyl or aryl units that may contain heteroatoms (S, N, O, Cl, Fe, Br or I), where b is an integer from 1 to 7 wherein any of the CH$_2$ groups in this unit may be substituted with alkyl or aryl units that may contain heteroatoms (S, N, O, Cl, Fe, Br or I), where R$^{16}$ is H or (CH$_2$)$_n$, where n in an integer from 1 to 6 or is a CH$_2$ linker unit that may be further substituted at any CH$_2$ group in the chain with alkyl or aryl units that may contain heteroatoms (S, N, O, Cl, F, Br, or I), 3) mixing the substituted or unsubstituted 2-pyridinol N-oxide material with the chelant such that the substituted or unsubstituted 2-pyridinol N-oxide material is present at between 0.0003 to 10% and the chelant is present at 0.005% to 15%.

BB) The method of example AA including the additional steps of providing an aqueous carrier and mixing the aqueous carrier with the substituted or unsubstituted 2-pyridinol N-oxide material and the chelant such that the aqueous carrier is present at 40% to 95% by weight of the mixture.

CC) The method of example AA including the additional steps of providing a surfactant and mixing the surfactant with the substituted or unsubstituted 2-pyridinol N-oxide material and the chelant such that the aqueous carrier is present at 20% to 95% by weight of the mixture.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
a) about 0.0003 to about 10% of a substituted or unsubstituted 2-pyridinol N-oxide material,
b) about 0.005 to about 15% of at least one chelant comprising Desferrioxamine,
c) from about 40% to about 95% aqueous carrier.

2. The personal care composition of claim 1 wherein the substituted or unsubstituted 2-pyridinol N-oxide material is present in the amount of about 0.0003% to about 2%.

3. The personal care composition of claim 1 wherein the chelant is present in the amount of about 0.005% to about 5%.

4. The personal care composition of claim 1 wherein the combination of the chelant and the substituted or unsubstituted 2-pyridinol N-oxide material increases the antibacterial efficiency of the substituted or unsubstituted 2-pyridinol N-oxide material at least about 50%.

5. The personal care composition of claim 4 wherein the combination of the chelant and the substituted or unsubstituted 2-pyridinol N-oxide material increases the antibacterial efficiency of the substituted or unsubstituted 2-pyridinol N-oxide material at least about 75%.

6. The personal care composition of claim 1 where the iron chelator has a log K$_1$ greater than about 16.

7. The personal care composition of claim 1 where the substituted or unsubstituted 2-pyridinol-N-oxide material comprises the molecular structure:

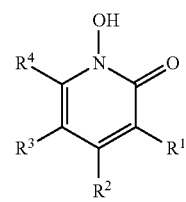

wherein R$^1$, R$^2$, R$^3$, R$^4$ are independently selected from the group consisting of H, Cl, Br, I, F, NO, NO$_2$, (CH$_2$)$_n$G, and mixtures thereof, wherein each G is independently selected from the group consisting of (O)$_m$SO$_3$M$^3$, (O)$_m$CO$_2$M$^3$, (O)$_m$C(O)(R$^5$), (O)$_m$C(O)N(R$^5$R$^6$), (O)$_m$CN, (O)$_m$(R$^5$), N(R$^5$R$^6$), and mixtures thereof, wherein m is 0 or 1, and wherein n is an integer from 0 to 4, and wherein R$^5$ and R$^6$ are independently selected from the group consisting of H and a substituted or unsubstituted C1-C12 organic group, and wherein M$^3$ is selected from the group consisting of H, a substituted or unsubstituted C$_1$-C$_{12}$, organic group, $^+$N(R$^7$R$^8$R$^9$R$^{10}$), and 1/q M' q+ wherein M' is selected from the group consisting of an alkali metal of charge q and an alkaline earth metal of charge q, where R7, R8, R9, and R10 are independently selected from the group consisting of H and a substituted or unsubstituted C$_1$-C$_{12}$, organic group, and wherein any pair of vicinal groups, R$^1$ and R$^2$, R$^2$ and R$^3$, R$^3$ and R$^4$, may be taken together to form another five- or six-membered aromatic or aliphatic ring optionally substituted with one or more groups selected from the group consisting of Cl, Br, I, F, NO, NO$_2$, CN, (CH$_2$)$_n$G, and mixtures thereof.

8. The personal care composition of claim 7, wherein each R$^1$ is independently selected from the group consisting of H, Cl, and (CH$_2$)nG, wherein G is independently selected from the group consisting of (O)mSO$_3$M, (O)mCO$_2$M, (O)mC(O)(R$^2$), (O)mCN, and (O)m(R$^2$), wherein each m is 0 or 1.

9. The personal care composition of claim 1, wherein said substituted or unsubstituted 2-pyridinol-N-oxide material is 1-hydroxy-4-methyl-6-(2,4,4-trimethylpentyl)-2-pyridone monoethanolamine salt.

10. The personal care composition of claim 1, wherein the chelant further comprises is-diethylenetriaminepentaacetic acid (DTPA).

11. The personal care composition of claim 1, wherein the chelant further comprises Diethylenetriaminepentakis (methylenephosphonic acid) (DTPMP).

12. The personal care composition according to claim 1, wherein the composition further comprises one or more additional antibacterial agents selected from the group consisting of carbanilides, triclocarban, triclosan, halogenated diphenylether, hexachlorophene, 3,4,5-tribromosalicylanilide, and salts of 2-pyridinethiol-1-oxide, salicylic acid, other organic acids, p-chloro-m-xylenol (PCMX), 4-Isopropyl-m-cresol (IPMP), Zinc pyrithione (ZPT), Benzalkonium chloride (BZK), Didecyl dimethyl ammonium chloride (DDAC), Hinokitiol, and combinations thereof.

13. The personal care composition according to claim 1, wherein the composition comprises a body wash.

14. The personal care composition according to claim 1, further comprising a detersive surfactant selected from the group consisting of ammonium lauryl sulfate, ammonium laureth sulfate, sodium lauryl sulfate, sodium laureth sulfate, sodium cocoyl isethionate, and combinations thereof.

15. The personal care composition according to claim 1, further comprising a benefit agent selected from the group consisting of petrolatum, glyceryl monooleate, mineral oil, natural oil, and combinations thereof.

* * * * *